(12) United States Patent
Florent et al.

(10) Patent No.: US 8,923,593 B2
(45) Date of Patent: Dec. 30, 2014

(54) SYSTEM AND METHOD FOR PRODUCING AN IMAGE OF A PHYSICAL OBJECT

(75) Inventors: Raoul Florent, Ville d'Avray (FR); Peter Willem Van Den Houten, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 122 days.

(21) Appl. No.: 13/636,132

(22) PCT Filed: Mar. 18, 2011

(86) PCT No.: PCT/IB2011/051137
§ 371 (c)(1),
(2), (4) Date: Sep. 20, 2012

(87) PCT Pub. No.: WO2011/117789
PCT Pub. Date: Sep. 29, 2011

(65) Prior Publication Data
US 2013/0011041 A1  Jan. 10, 2013

(30) Foreign Application Priority Data

Mar. 24, 2010 (EP) .................................... 10305293

(51) Int. Cl.
*G06K 9/00* (2006.01)
*G06T 7/00* (2006.01)

(52) U.S. Cl.
CPC ....... *G06T 7/003* (2013.01); *G06T 2207/10121* (2013.01); *G06T 2207/20224* (2013.01); *G06T 2207/30052* (2013.01); *G06T 2207/30101* (2013.01); *G06T 2207/30204* (2013.01)

USPC ......................................................... 382/132

(58) Field of Classification Search
None
See application file for complete search history.

(56) References Cited

U.S. PATENT DOCUMENTS

| 7,415,169 B2 | 8/2008 | Florent et al. |
| 2007/0016108 A1 | 1/2007 | Camus et al. |
| 2009/0169080 A1 | 7/2009 | Noordhoek |

FOREIGN PATENT DOCUMENTS

| DE | 102007023719 | 9/2008 |
| WO | WO2004044847 | 5/2004 |
| WO | WO2006077534 | 7/2006 |

*Primary Examiner* — Nirav G Patel

(57) ABSTRACT

The invention relates to a system and a method for producing an image of a physical object and to a computer program element and a computer readable medium. In order to provide improved stent boost subtract also showing wire state information, a system and a method are provided, the method comprising the following steps: a) tracking a predetermined first feature (126) and a predetermined second feature (128) in a first plurality (114) of first images (116), which images reveal a first criterion (118); and determining a first feature transform; and determining second feature distortion vector fields relative to the first feature transform; b) associating and recording second feature distortion vector fields corresponding to at least two phase attributes (120); c) tracking the predetermined first feature (126) in at least one secondary image (142) which image reveals a second criterion; d) determining a first-feature-based inter-criterion the first-feature-based inter-phase transform and the second feature distortion vector fields corresponding to a matching phase attribute (120); and f) generating a combined inter-criterion image (162) based on the restored physical distortion.

25 Claims, 9 Drawing Sheets

SYSTEM AND METHOD FOR PRODUCING AN IMAGE OF A PHYSICAL OBJECT

FIELD OF THE INVENTION

The invention relates to producing an image of a physical object. In particular, the invention relates to a system and a method for producing an image of a physical object and to a computer program element and a computer readable medium.

BACKGROUND OF THE INVENTION

Methods for producing an image of a physical object are widespread in several technical fields, e.g. in the medical field. One example in the medical field for visualizing a physical object in an image is the field of coronary stents. For providing a user, e.g. a physician or a surgeon or an interventional cardiologist, information about whether the stent is in a correct position or whether the stent is correctly expanded and well apposed to the vessel walls, an image of the stent is produced and provided that is displayed to the user. It is very important to determine whether or not a stent is correctly deployed since incorrect deployment or partial expansion is a strong factor of re-stenosis or late thrombosis. In addition, when, for example, so-called drug-eluted stents are used, complete apposition is mandatory since the struts of the stent are coated with a drug that slowly diffuses in the vessel tissues in order to prevent over cicatrisation. In case of incorrect deployment, the ill-apposed struts will not be able to deliver their preventive treatment. However, for example, a stent is not always clearly visible under fluoroscopy or even in an exposure (cine) run. It is therefore known to improve stent visibility in X-ray exposures to facilitate the interventional cardiologist, for example, in judging the present situation. A first step is the so-called StentBoost® technique, which first realization relied on balloon marker detection for the registration and temporal boosting of a set of images containing the stent prior deployment. From DE 10 2007 023 719 A1, an improvement of the stent boost technique is described, which improvement is also called stent boost subtract. In stent boost subtract, simply spoken, a traditional stent boosted image realized prior contrast agent injection is registered and merged with a vessel image acquired after contrast agent injection. But it has been shown that in stent boost subtract, a disadvantage lies in the fact that it is impossible to detect or to track the wire under contrast agent, which wire reflects by its shape the real bending of a stent, which is in particular of importance when applying stents with a rather long extension.

SUMMARY OF THE INVENTION

Hence, there may be a need to provide an improved stent boost subtract also showing wire state information.

According to an exemplary embodiment, a method for producing an image of a physical object is provided comprising the following steps:

a) tracking a predetermined first feature and a predetermined second feature in a first plurality of first images, which images reveal a first criterion; and determining a first feature transform; and determining second feature distortion vector fields relative to the first feature transform;

b) associating and recording second feature distortion vector fields corresponding to at least two phase attributes;

c) tracking the predetermined first feature in at least one secondary image which image reveals a second criterion;

d) determining a first-feature-based inter-criterion transform;

e) restoring current physical distortion by composing the first-feature-based inter-phase transform and the second feature distortion vector fields corresponding to a matching phase attribute; and f) generating a combined inter-criterion image based on the restored physical distortion.

According to an exemplary embodiment, a method is provided,
wherein step a) comprises as sub-steps:

a1) receiving the first plurality of first images revealing the first criterion; identifying and recording the phase attribute for each image of the first plurality of first images;

a2) detecting at least the predetermined first and the predetermined second feature in each image of the first plurality of first images and determining the location of the first feature;

a3) tracking the first and second features in each image of the first plurality of first images, and registering those images to one of the first images, which one image is determined as a reference image, said registration being calculated so that it corresponds to the spatial matching of the first and second features of each first image with the first and second features of the reference image; wherein the registration is achieved with restoration fields;

a4) decomposing the restoration fields into a combination of an affine transform and a relative warping transform; and a5) generating an integrated first image by integrating at least two images of the first plurality of first images; wherein the integration is a temporal integration; and wherein the at least two images are motion-compensated;

wherein step b) comprises recording the relative warping transform instances as the second feature distortion vector fields and tagging them with a corresponding phase attribute; wherein a warping map is created;

wherein step c) comprises the following sub-steps:

c1) receiving the at least one secondary image revealing a second criterion; wherein a phase attribute is identified and recorded for the at least one secondary image; and c2) detecting the first feature in the at least one secondary image and tracking the first features by determining their locations;

wherein step d) comprises computing the first-feature-based inter-criterion transform for bringing the first features in the integrated image and the first features in the at least one secondary image into correspondence with each other along time; wherein the computing is based on the locations of the first features determined in step a) and the locations of the first features tracked in step c);

wherein, for restoring the current physical distortion, step e) comprises generating a restoration transform by associating one of the recorded relative warping transform instances of the warping map with a phase attribute matching the phase attribute of the at least one secondary image and composing the associated relative warping transform with the computed first-feature-based inter-criterion transform; and wherein step f) comprises generating the combined inter-criterion image by combining the integrated first image and the at least one secondary image, wherein at least one of the integrated first image and the at least one secondary image has been transformed according to the generated restoration transform.

According to an exemplary embodiment, a system for producing an image of a physical object, the system comprising an image acquisition device, and a processing arrangement which comprises a tracking unit, an association unit, a determination unit, a restoration unit and a generation unit.

The image acquisition device is adapted to acquire a first plurality of first images revealing a first criterion and to acquire at least one secondary image revealing a second criterion.

The tracking unit is adapted to track a predetermined first feature and a predetermined second feature in a first plurality of first images, which images reveal a first criterion; and to track the predetermined first feature in at least one secondary image which image reveals a second criterion. The determination unit is adapted to determine a first feature transform; to determine second feature distortion vector fields relative to the first feature transform; and to determine a first-feature-based inter-criterion transform. The association unit is adapted to associate and record second feature distortion vector fields corresponding to at least two phase attributes. The restoration unit is adapted to restore current physical distortion by composing the first-feature-based inter-phase transform and the second feature distortion vector fields corresponding to a matching phase attribute. The generation unit is adapted to generate a combined inter-criterion image based on the restored physical distortion.

According to an exemplary embodiment, the processing arrangement is adapted to receive the acquired first plurality of first images revealing the first criterion and to identify and record a phase attribute for each image of the first plurality of images; to detect at least the predetermined first and the predetermined second feature in each image of the first plurality of first images and to determine the location of the first feature; to track the first and second features in each image of the first plurality of first images and to register those images to one of the first images, which one image is determined as a reference image, said registration being calculated so that it corresponds to the spatial matching of the first and second features of each first image with the first and second features of the reference image; wherein the registration is achieved with restoration fields; to decompose the restoration fields into a combination of an affine transform and a relative warping transform; to record the relative warping transform instances and to tag them with a corresponding phase attribute, wherein a warping map is created; to generate an integrated first image by integrating at least two images of the first plurality of first images, wherein the integration is a temporal integration; and wherein the at least two images are motion-compensated; to receive the at least one secondary image revealing the second criterion and to identify and record a phase attribute for the at least one secondary image; to detect the first feature in the at least one secondary image and to track the first features by determining their locations; to compute a first-feature-based inter-criterion transform for bringing the first features in the integrated image and the first features in the at least one secondary image into correspondence with each other along time, wherein the computing is based on the locations of the first features determined before and the locations of the first features tracked before; to generate a restoration transform, for restoring the current physical distortion, by associating one of the recorded relative warping transform instances of the warping map with a phase attribute matching the phase attribute of the at least one secondary image and composing the associated relative warping transform with the computed first-feature-based inter-criterion transform; and to generate the combined inter-criterion image by combining the integrated first image and the at least one secondary image, wherein at least one of the integrated first image and the at least one secondary image has been transformed according to the generated restoration transform.

Among others, the above described method and system provide the advantage that an image is generated containing information about both the predetermined first features and the predetermined second features. Although only the first features are detectable in the secondary image, the combined inter-criterion image also reflects the motion of the predetermined second features as they are present in the secondary image by applying the restoration based on the warping map derived before.

Since the first images reveal the first criterion and the at least one second image reveals the second criterion, the term "combined inter-criterion image" refers to the fact that the combined image is based on transform information and image data from both criteria.

The term "inter-criterion" refers to computing the transform of the first feature of the first images revealing the first criterion with respect to the second images revealing the second criterion.

According to an exemplary embodiment, in step a3), the registration is achieved with elastic restoration fields.

According to an exemplary embodiment, in step a4), the elastic restoration fields are decomposed into a combination of an affine transform and a relative elastic warping transform.

According to an exemplary embodiment, in step a5), the at least two images are elastically motion-compensated.

According to an exemplary embodiment, step b) comprises the recording of relative elastic warping transform instances as the second feature distortion vector fields.

According to an exemplary embodiment, in step e), the restoration transform is generated by associating one of the recorded relative elastic warping transform instances of the warping map with a phase attribute matching the phase attribute of the at least one secondary image and composing the associated relative elastic warping transform with the computed first-feature-based inter-criterion transform.

According to an exemplary embodiment, in the at least one secondary image, the second feature is not detectable.

According to an exemplary embodiment, the generation of the integrated first image (step a5)) is based on the result of the tracking and registration (step a3)). For example, the temporal integration is directly applied on the registered images of step a3).

According to an exemplary embodiment, the restoration transform is a distortion restoration transform.

According to an exemplary embodiment, the first plurality of images comprises at least two images.

According to another aspect of an exemplary embodiment, the first plurality of images comprises a sequence of images of a region of interest of an object comprising the physical object.

According to an exemplary embodiment, the first plurality of first images and the at least one secondary image are X-ray images.

According to another aspect of an exemplary embodiment, the images are acquired by an X-ray acquisition device such as a C-arm type X-ray acquisition or a CT.

According to another aspect of an exemplary embodiment, the first criterion refers to a first phase without injected contrast agent and wherein the second criterion refers to a second phase with injected contrast agent.

According to another aspect of an exemplary embodiment, a detector is provided for separating the first phase without injected contrast agent from the second phase with injected contrast agent.

According to an exemplary embodiment, a threshold is predetermined for the separation.

For facilitating the procedure, the separation of the first phase and the separation of the second phase can be achieved automatically.

An automatic detection is, for example, possible by detecting the contrast agent arrival when injecting contrast agent.

However, as a result, when applying the system and method according to the invention in, for example, intracoronary interventions where stents are inserted into a vessel system, the invention is detectable since the result combines the stent boost subtract results in a visible manner on an image with the wire based warping shown, which is measurable and thus the invention detectable.

According to an exemplary embodiment, the phase attribute comprises an attribute relating to a cardiac phase of the object.

By providing a cardiac phase identifier, preferably all along the process, that is before and after the contrast agent injection for example, the cardiac phase corresponding to each considered image or frame can be identified. For example, this identification can either rely on image analysis, for instance, since markers are detected, the trajectories of those markers can be analyzed so as to separate the cardiac motions from the respiratory motions, or the identification can be derived from external means such as an ECG.

By identifying and recording a phase attribute, it is possible to tag or index each frame or image of a sequence of images with a cardiac phase index.

According to another aspect of an exemplary embodiment, the predetermined first feature comprises a marker.

According to another aspect of an exemplary embodiment, the predetermined first feature comprises at least two markers.

According to another aspect of an exemplary embodiment, the predetermined second feature comprises a wire.

According to another aspect of an exemplary embodiment, the predetermined second feature comprises a guide-wire or balloon wire or monorail delivering device for a stent implanting procedure.

According to another aspect of an exemplary embodiment, the predetermined second feature comprises a stent.

According to another aspect of an exemplary embodiment, the elastic restoration fields comprise elastic transforming.

According to another aspect of an exemplary embodiment, the first of the first plurality of first images is determined for the reference image According to another aspect of an exemplary embodiment, an affine transform is composed of linear transformations and a translation.

For example, the linear transformations comprise rotation, scaling and/or shear. The translation comprises a shifting motion.

According to another aspect of an exemplary embodiment, warping comprises a transforming process that at least partially corrects restorations such as distortion restorations in the image.

According to an exemplary embodiment, warping comprises morphing which defines a change of a first image into a second image by applying a seamless transition.

According to an exemplary embodiment, the full image is warped. The registration transform that matches the markers and the wire is only really unambiguously defined for those image points corresponding to the matched points (the markers and wire points). Therefore, for example, the transform is extended to other non-feature points in the image. For instance, it is possible to map two couple of markers with many transforms (i.e. an infinity); but there are only several possible affine transforms among which the steps translation+rotation+scaling in the direction of the inter-marker segment are chosen. But once defined, the affine transform applies over the full image. For the wire, the situation is identical, but more complex, because it is not possible to resort to the notion of affine transform in this case. Hence, a "natural extension" of a transform defined on sparse points to a full dense space is required, which, for example, is achieved by the rigid transform.

During the first phase images, in other words during the pre-contrast agent sequence, the elastic restoration fields corresponding to the matching of the wire and marker couple during this phase are recorded and tagged with the corresponding cardiac phases. This creates the above-mentioned warping map that is indexed by the cardiac phases. But, before storing those elastic transforms, they are decomposed into the combination of an affine transform, which is the transform matching the markers, plus a relative elastic warping, which is the elastic warping that remains once the affined transform has been corrected for.

The warping map provides a set of Ry, which can also be referred to as $\{R\phi_t\}$.

If Wt is the full elastic transform matching the wires along time, and if At is the affine transform matching the markers along time, then the relative elastic warping transform is defined as $Rt=Wt*At^{-1}$.

This is stored as a function of the cardiac phase $R\phi_t$.

According to an exemplary embodiment, when building the map, the corresponding relative elastic transforms are averaged, for example in case several images, i.e. images corresponding to the non-consecutive frame indices $t_A$, $t_B$ etc., correspond to the same phase value $\phi$. As an advantage, only one transform for entry $\phi$ is obtained that accounts for images $t_A$, $t_B$ etc.

According to another aspect of an exemplary embodiment, an affine transformation excluding scaling is a rigid transform.

According to an exemplary embodiment, the integrated first image is a wire-based StentBoost ® image.

For example, the integrated first image is achieved by using the pre-contrast agent injected images and using the wire and marker couple tracking results. This produces an image or a sequence of images containing the boosting stent that has been obtained through elastically motion compensated temporal integration.

According to an exemplary embodiment, step c2) comprises marker tracking.

After contrast agent injection, the wire becomes invisible under contrast agent. However, the markers are still visible and can be correctly tracked with refined versions of the marker detection methods used in step C, mentioned above.

According to another aspect of an exemplary embodiment, step e) is performed such as to achieve affine transforming.

According to an exemplary embodiment, with the computing of the restoration transform, the warping map accounts for elastic transforming and the computed first-feature-based inter-criterion transform accounts for affine transforming.

In other words, first, based on the current cardiac phase and using the pre-contrast agent warping map, it is possible to retrieve the corresponding elastic transform. However, what is retrieved from the warping map is the relative elastic transform $R\phi_a$. This transform is composed with the current marker matching transform At to form the restoration field: $R\phi_a*At$.

Equipped with this elastic transform, which is applied, for example, on the current contrast agent injected image, and after a combination with the pre-contrast agent boosted image or images, it is possible to generate or produce a final image (or images) which is (are) also referred to, according to the invention, as a wire based stent boost subtract result.

According to another aspect of an exemplary embodiment, the object is a patient and the region of interest relates to heart vessels and wherein the affine transform compensates for breathing motion and for translational heart motion and wherein the elastic transforming compensates for bending motion due to heart motion.

According to another aspect of an exemplary embodiment, step a5) is carried out after step a1) but before step f).

According to another aspect of an exemplary embodiment, step a5) is carried out before or parallel to the sequence of steps a2) to a4).

According to another aspect of an exemplary embodiment, step b) is carried out before step e).

However, the arrangement of a particular order when to perform which steps can be adapted in order to provide an optimized performance of the particular system used with the invention. For example, in case a result is needed as instantly as possible, the computational steps can be performed parallel on an adapted system with a processing arrangement or processing unit adapted for performing several computational operations in the same time in order to provide the results from the sub-steps in the fastest time possible thus leading to a near real-time result of the displayed image, for example the wire based stent boost subtract result.

According to another aspect of an exemplary embodiment, the combined inter-criterion image is displayed to a user.

According to another aspect of an exemplary embodiment, the physical object is a stent.

According to another aspect of an exemplary embodiment, the phase attribute relates to a cardiac phase.

According to another aspect of an exemplary embodiment, the first feature are markers present in the first plurality of first images and in the at least one secondary image, wherein the second features are guide-wires of a stent.

According to another aspect of an exemplary embodiment, step f) comprises fusing the two images.

According to a further aspect, fusing comprises subtracting.

As an example, the term subtracting is used for adding one image to the other. As a further example, the term subtracting refers to subtracting one image from the other.

According to another aspect of an exemplary embodiment, fusing comprises overlaying.

According to another aspect of an exemplary embodiment, fusing comprises displaying in a spatial or temporal interlaced way.

According to an exemplary embodiment, in step f) the integrated first image is transformed according to the generated restoration transform; and wherein the transformed integrated first image is combined with the at least one secondary image.

This provides the advantage that the present or actual situation presented in the secondary image, for example a contrast agent injected image, shows the situation to the user in a so-called real world environment, i.e. in an X-ray image, such as a fluoroscopy image, for example. Because this secondary image has not been further transformed, the detailed contents shown in the X-ray image, for example, are not further affected and can thus be easily be percepted by the user.

According to another aspect of an exemplary embodiment, in step f) the at least one secondary image is transformed according to the generated restoration transform; and wherein the transformed at least one secondary image is combined with the integrated first image.

According to another aspect of an exemplary embodiment, in step f) the at least one secondary image and the integrated image are transformed according to the generated restoration transform; and wherein the transformed images are combined with each other.

According to an exemplary embodiment, the at least one secondary image and the integrated image are each transformed with a predetermined ratio of the generated restoration transform.

This provides the possibility to transform both images in such a way that the result can be adapted to provide an image with an optimum perceptibility, that is an image which the user, for example a clinical staff such as a surgeon, finds easily to read and to interpret the features shown in the image. For example, in case the secondary image itself shows a rather distorted or not so easy to read situation, and at the same time also the integrated image is in a certain way not so easy to understand, it might be advisable to find a virtual intermediate transformation to match both images.

According to an exemplary embodiment, before step e) at least two recorded relative elastic warping transform instances of the warping map are interpolated according to the phase attribute of the at least one secondary image.

The interpolation provides the advantage to arrive at enhanced relative elastic warping transform instances, or values, without the need to generate a warping map with a high resolution, in other words, it is not necessary to generate a large plurality of relative elastic warping transform instances for the map. For example, in case several secondary images are recorded and one of these images is selected because it provides the best visibility of the second features, the markers for example, and with this chosen image has a phase attribute, for example a cardiac phase index, which does not directly match with a phase attribute of one of the instances, or values, stored in the warping map, the interpolation generates the so to speak missing instance, or value, in order to provide a restoration, which is based on the correct association of the phase attributes, with the highest preciseness as possible. This also allows getting good warping results even with a low resolution warping map, which could occur if the image acquisition rate during the first phase is limited. This allows working with lower frame rates, which correspond to lower X-ray dose.

According to an exemplary embodiment, the term instance refers to "value" in a broad sense.

According to an exemplary embodiment, the transform is defined by parameters. According to another exemplary embodiment, the transform is defined by a full vector field.

According to an exemplary embodiment, before step c1) a second plurality of secondary images according to the second criterion is acquired; and wherein at least one image of the second plurality is selected as the at least one secondary image.

This provides the possible to choose a secondary image where the first features, for example the markers, are easily detectable. This also implies the advantage that the dose necessary for acquiring the image, for example with an X-ray image acquisition device, can be reduced which is a great relief for both the patient and the clinical staff.

According to an exemplary embodiment, step f) comprises combining the images in a merging manner with a varying fading factor over a period of time.

According to another aspect of an exemplary embodiment, merging comprises continuously showing one of the images while periodically fading in and out of the other one of the images.

According to an exemplary embodiment, the at least one secondary image is continuously shown and the transformed integrated first image is periodically fading in and out.

By fading in and out of the integrated first image, for example a wire based stent boost image, or a pre-boosted stent image, it is possible to show the secondary image with all its information without any covering by the combination with the pre-boosted stent image itself. In other words, the user is provided with the information shown in the secondary image, for example a contrast agent injected image, where detailed information is shown about the vessels structure and the situation of the vessel whereas only the first features, for example the markers, are shown. By fading in the integrated first image, this additional information is, for example, overlaid or added to the secondary image, thus covering at least partially some of the information shown in the original secondary image. But the user having seen the secondary image before has the information already received such that it is possible for him or her to understand the situation in an enhanced way by combining the, for example, pre-boosted stent image with the full information content of the secondary image.

In another example, in case the user is used to read pre-boosted stent images, it is also possible to arrange a fading between the pre-boosted stent image and the secondary image, wherein care has to be taken that a restoration transform has been applied to either one of the images such that both images show the same restoration, or transformed state, so that starting from a transformed pre-boosted stent image, for example, the secondary image is continuously increasingly shown to an extent where both images are probably fused with each other and then the pre-boosted stent image is fading out such that the secondary image is shown without the pre-boosted stent image. Of course, then the fading in and out process can be applied in a reverse manner so as to provide a cine-loop-like image sequence.

According to another aspect of an exemplary embodiment, the integrated first image is continuously shown and the transformed at least one secondary image is periodically fading in and out.

According to another aspect of an exemplary embodiment, the transformed at least one secondary image is continuously shown and the transformed integrated first image is periodically fading in and out.

According to another aspect of an exemplary embodiment, the transformed integrated first image is continuously shown and the transformed at least one secondary image is periodically fading in and out.

According to another aspect of an exemplary embodiment, the first plurality of first images is acquired for at least one heart cycle; wherein several different integrated first images are generated for different phases of the heart cycle; and wherein a second plurality of secondary images is acquired for at least one heart cycle; and wherein combined inter-criterion images are generated for different phases of the heart cycle. This allows talking into account the motion dynamics and to observe the temporal deformation of the vessel and endo-prothesis.

According to another aspect of an exemplary embodiment, the combined inter-criterion images are displayed as a cine-loop.

According to an exemplary embodiment, the system comprises a display adapted to display the combined inter-criterion image.

According to an exemplary embodiment, the image acquisition device is an X-ray image acquisition device; and wherein the first plurality of first images and the at least one secondary image are X-ray images.

According to an exemplary embodiment, the processing arrangement unit is adapted to interpolate at least two recorded relative elastic warping transform instances of the warping map according to the phase attribute of the at least one secondary image.

According to another aspect of an exemplary embodiment, the processing arrangement is adapted to transform the integrated first image according to the generated restoration transform; and to combine the transformed integrated first image with the at least one secondary image.

According to another aspect of an exemplary embodiment, the image acquisition device is adapted to acquire a second plurality of secondary images according to the second criterion; and wherein the processing arrangement is adapted to select at least one image of the second plurality as the at least one secondary image.

According to another aspect of an exemplary embodiment, the processing arrangement is adapted to combine the images for the combined inter-criterion image in a merging manner with a varying fading factor over a period of time.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

It has to be noted that exemplary embodiments of the invention are described with reference to different subject matters. In particular, some exemplary embodiments are described with reference to apparatus type claims whereas other exemplary embodiments are described with reference to method type claims. However, a person skilled in the art will gather from the above and the following description that, unless other notified, in addition to any combination of features belonging to one type of subject matter also any combination between features relating to different subject matters, in particular between features of the apparatus type claims and features of the method type claims is considered to be disclosed with this application.

BRIEF DESCRIPTION OF THE DRAWINGS

The aspect defined above and further aspects, features and advantages of the present invention can also be derived from the examples of embodiments to be described herein after and are explained with reference to examples of embodiments, but to which the invention is not limited. The invention will be described in more detail hereinafter with reference to the drawings.

FIG. 2b schematically shows a further exemplary embodiment of the method of FIG. 2a;

DETAILED DESCRIPTION OF EMBODIMENTS

Figure 1:
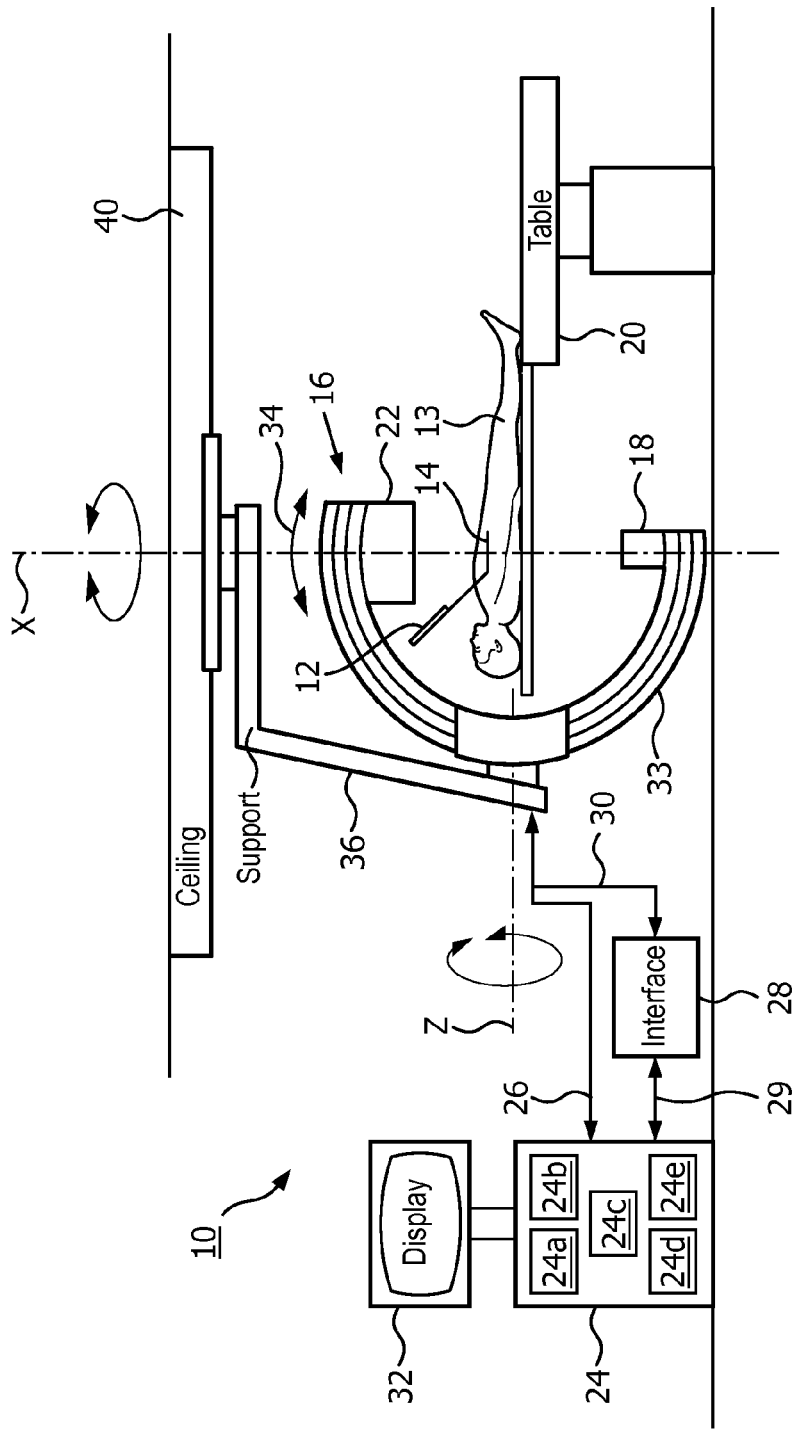
FIG. 1 schematically shows a system for producing an image of a physical object according to the invention.

FIG. 1 schematically shows a system 10 for producing an image of a physical object, for example a stent inserted by an interventional device 12 in a vessel, for example a cardiac vessel, of a patient 14. As an example, the interventional device 12 is a guide wire for inserting the stent.

The system 10 comprises an X-ray image acquisition device 16 with a source of X-ray radiation 18 provided to generate X-ray radiation. A table 20 is provided to receive a subject to be examined, for example the patient 14. Further, the X-ray image acquisition device 16 comprises a detection module 22 located opposite the source of X-ray radiation 18. During the radiation procedure, the subject or patient 14 is located between the source of X-ray radiation 18 and the detection module 22. The latter is sending data to a control unit or processing arrangement 24 connected to the X-ray image acquisition device 16 by a cable connection 26. Of course, the cable connection 26 can also be provided in form of a wireless connection (not shown). The interventional device 12 is connected to an interface 28, which connection is not shown in FIG. 1 and which can be implemented also as a wire based or as a wireless connection. The interface 28 is connected to the processing arrangement 24 and the X-ray image acquisition device 16 by connections 29 and 30 respectively. Further, a display 32 is connected to the processing arrangement 24.

The X-ray image acquisition device 16 is provided as a so-called C-type X-ray image acquisition device where the X-ray source 18 and the detection module 16 are arranged on opposing ends of a C-arm 32. The C-arm 32 is rotatably mounted around a horizontal axis indicated as z-axis. The C-arm can further be rotated in a circular or semi-circular form indicated by an arrow 34. Furthermore, according to the example shown, the C-arm 32 is mounted to a support 36 suspended from a sealing 40, wherein the support is rotatable around a vertical axis indicated as x-axis. Thus, X-ray images can be acquired from different directions of different regions of interest of the patient 14. The interface device 28 is arranged to input information or commands by the user. The interface device 28 is also adapted to connect the processing unit and thus also the X-ray image acquisition device with other devices, if this is required by the user, for example because of a complex medical intervention.

It is noted that the example shown as a CT-type X-ray image acquisition device, although the invention also relates to other types of X-ray image acquisition devices, such as CT-systems. Of course, as an X-ray image acquisition device, a much more simplified C-arm device or even a stationary X-ray image acquisition device which is not movable around a patient, can be used instead of the one shown in FIG. 1.

The X-ray image acquisition device 16 is adapted to acquire a first plurality of first images revealing a first criterion and to acquire at least one secondary image revealing second criterion.

The processing arrangement 24 comprises a tracking unit 24a, an association unit 24b, a determination unit 24c, a restoration unit 24d and a generation unit 24e. The tracking unit 24a is adapted to track a predetermined first feature and a predetermined second feature in a first plurality of first images, which images reveal a first criterion. The tracking unit 24a is also adapted to track the predetermined first feature in at least one secondary image which image reveals a second criterion. The determination unit 24c is adapted to determine a first feature transform and to determine second feature distortion vector fields relative to the first feature transform. The determination unit 24c is also adapted to determine a first-feature-based inter-criterion transform. The association unit 24b is adapted to associate and record second feature distortion vector fields corresponding to at least two phase attributes. The restoration unit 24d is adapted to restore current physical distortion by composing the first-feature-based inter-phase transform and the second feature distortion vector fields corresponding to a matching phase attribute. Further, the generation unit 24e is adapted to generate a combined inter-criterion image based on the restored physical distortion.

According to an exemplary embodiment, not further shown, the processing arrangement 24 is adapted to receive the acquired first plurality of first images revealing a first criterion and to identify and record a phase attribute for each image of the first plurality of images. The processing arrangement 24 is also adapted to detect at least a predetermined first and a predetermined second feature in each image of the first plurality of first images and to determine the location of the first feature and to track; to track the first and second features in each image of the first plurality of first images and to register those images to one of the first image, which one image is determined as a reference image, said registration being calculated so that it corresponds to the spatial matching of the first and second features of each first image with the first and second features of the reference image; wherein the registration is achieved with elastic warping fields. The processing arrangement 24 is further adapted to decompose the elastic restoration fields into a combination of an affine transform and a relative elastic warping transform. Furthermore, the processing arrangement 24 is adapted to record the relative elastic warping transform instances or values and to tag them with a corresponding phase attribute, wherein a warping map is created, and to generate an integrated first image by integrating at least two images of the first plurality of first images, wherein the integration is a temporal integration, and wherein the at least two images are elastically motion-compensated. The processing arrangement 24 is also adapted to receive the at least one secondary image and to identify and record a phase attribute for the at least one secondary image and to detect the first feature in the at least one secondary image and to track the first features by determining their locations. The processing arrangement 24 is still further adapted to compute a first-feature-based inter-criterion transform for bringing the first features in the integrated image and the first features in the at least one secondary image into correspondence with each other along time, wherein the computing is based on the locations of the first features determined before and the locations of the first features tracked before and to generate a restoration transform by associating one of the recorded relative elastic warping transform instances, or values, of the warping map with a phase attribute matching the phase attribute of the at least one secondary image and combining the associated relative elastic warping transform with the computed first-feature-based inter-criterion transform. The processing arrangement 24 is finally also adapted to generate a combined inter-criterion image by combining the integrated first image and the at least one secondary image, wherein at least one of the integrated first image and the at least one secondary image has been transformed according to the generated restoration transform.

The procedure according to the invention to be used with the above-described system 10 is described in more detail below.

Figure 2A:
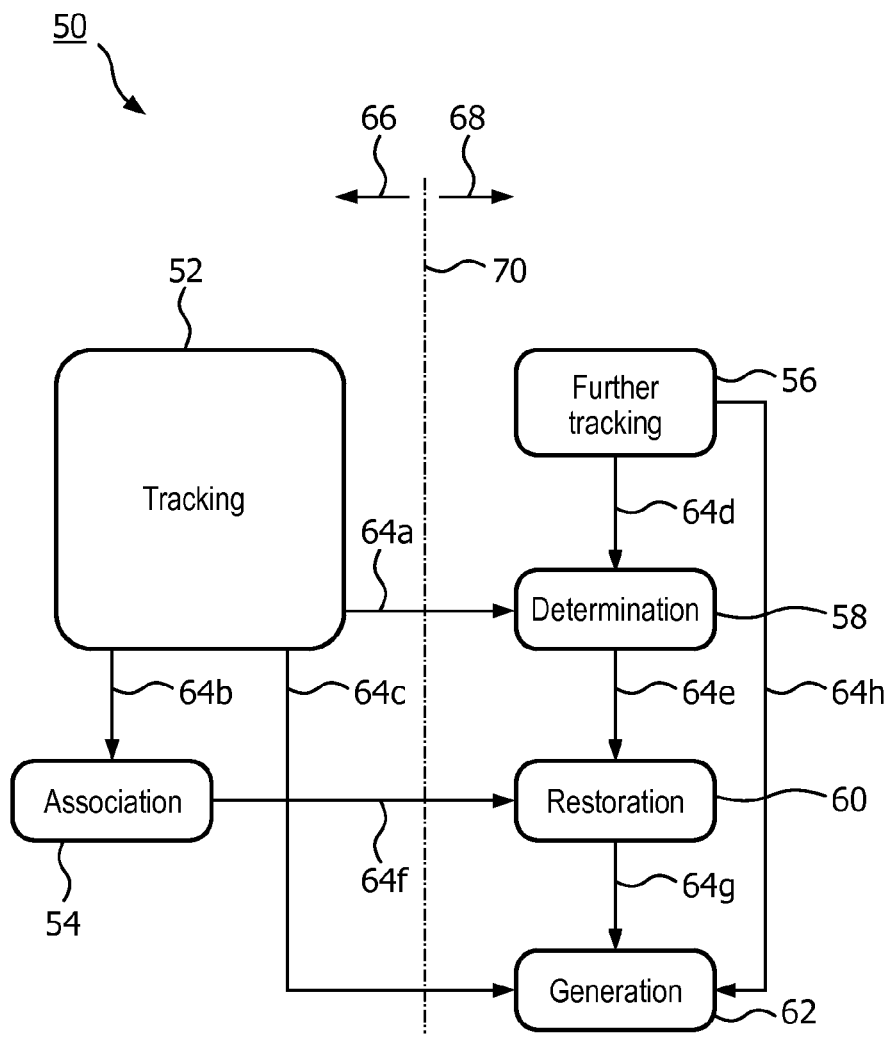
FIG. 2a schematically shows the basic steps of an exemplary embodiment of a method for producing an image of a physical object according to the invention.

FIG. 2a shows an exemplary embodiment of a method 50 for producing an image of a physical object, comprising the following steps:

First, in a tracking step 52, a predetermined first feature and a predetermined second feature in a first plurality of first images are tracked, which images reveal a first criterion. Also, a first feature transform and second feature distortion vector fields relative to the first feature transform are determined. Next, in an association step 54, second feature distortion vector fields corresponding to at least two phase attributes are associated and recorded. In a further tracking step 56, the predetermined first feature in at least one secondary image is tracked, which image reveals a second criterion. Then, in a determination step 58, a first-feature-based inter-criterion transform is determined. Further, in a restoration step 60, current physical distortion is restored by composing the first-feature-based inter-phase transform and the second feature distortion vector fields corresponding to a matching phase attribute. Then, in a generation step 62, a combined inter-criterion image based on the restored physical distortion is generated. The input and relation of the steps are indicated by arrows 64 pointing from a previous step to a following or dependent step showing the direction of influence or input. For example, the first criterion, not further shown in FIG. 2a, is revealed in the images in a first time period, or part according to time, indicated by an arrow 66 and the second criterion is revealed in the images in a second time period, or part according to time, indicated by an arrow 68. This is also indicated by a line 70 dividing the diagram in a left or first part and a right or second part.

In the example shown, the arrows represent image links, or transform links, or feature links. For example, an arrow 64a branching from 52 to 58 indicates a feature link. An arrow 64b branching from 52 to 54 indicates a transform link. An arrow 64c branching from 52 to 62 indicates an image link. An arrow 64d branching from 56 to 58 indicates a feature link. An arrow 64e branching from 58 to 60 indicates a transform link. An arrow 64f branching from 54 to 60 indicates a transform link. An arrow 64g branching from 60 to 62 indicates a transform link. An arrow 64h branching from 56 to 62 indicates an image link.

According to an exemplary embodiment, the arrow 64a may represent first criterion markers as first features in a reference image, e.g. a pre-contrast-agent time phase as first criterion, with a wire of a stent as second features.

The arrow 64b may represent a relative-elastic transform between any phase attribute, such as a cardiac phase, and the reference image. The arrow 64c may represent a so-called stent boosted image (for further explanation of this term, also see below).

The arrow 64d may represent markers as first features in second criterion current image, for example a contrast-agent time phase as second criterion.

The arrow 64e may represent an affine transform between a current image and a reference image.

The arrow 64f may represent relative-elastic transform between current cardiac phase and the reference image.

The arrow 64g may represent a composition of a relative-elastic transform with affine transforms.

The arrow 64h may represent bringing a current image to the generation step referenced by 62.

In the example shown in FIG. 2a, a phase attribute such as cardiac phases may be provided throughout the steps.

Figure 2B:
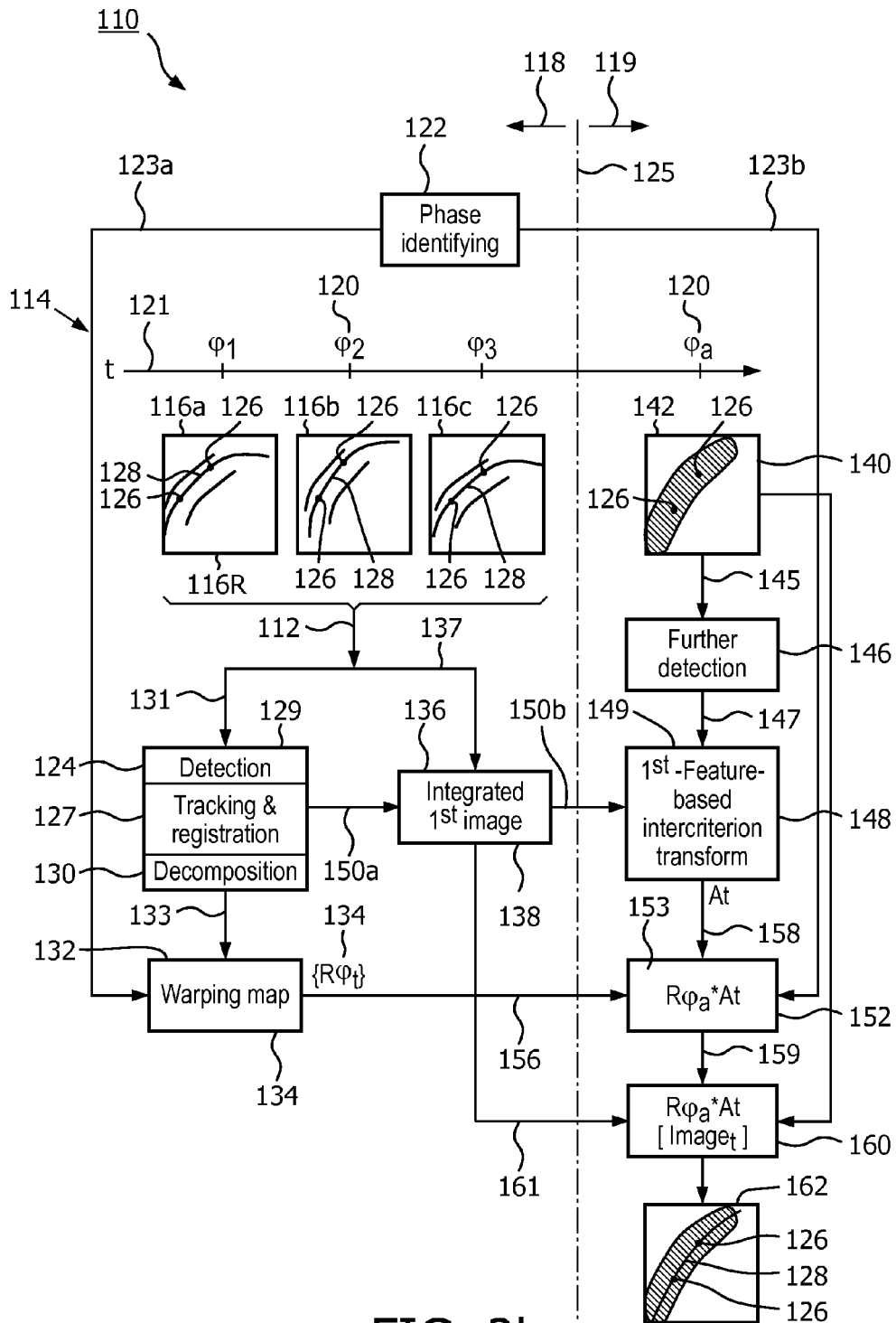

As can be seen from FIG. 2b, another exemplary embodiment provides a method 110 for producing an image of a physical object comprising the following steps:

First, in a reception step 112, a first plurality 114 of first images 116a, 116b, 116c revealing a first criterion 118 is received. A phase attribute 120 is identified by a phase attribute identifying step 122 and recorded for each image of the first plurality 114 of images 116a,b,c.

The identification of a phase attribute 120 along time t is indicated by a time line 121.

The provision of a phase attribute 120 to further steps is indicated by arrows 123a and 123b leading from the box indicating the phase attribute identifying step 122 to other steps (see below).

For example, the first plurality 114 of images comprises a sequence of images of a region of interest of an object comprising the physical object. For example, the object is a patient 14, wherein the physical object is a stent inserted into a vessel of the patient.

As an example, the first criterion 118 refers to a first phase without injected contrast agent where the first plurality 114 of images is acquired. A second criterion 119 refers to, for example, a second phase with injected contrast agent.

The separation of the two phases is indicated in FIG. 2b with a dashed line 125 dividing the diagram into a left half referring to the first criterion 118, or in other words, to the phase where no contrast agent is injected. The right part of FIG. 2b on the right side of the line 125 refers to the second phase with the second criterion 119 in which contrast agent has been injected.

For separation of the two phases, a detector can be provided which detector separates the first phase without injected contrast agent from the second phase with injected contrast agent on behalf of a predetermined threshold. For example, the detector (not shown) detects the arrival of the bolus of contrast agent once the contrast agent has been injected.

The phase attribute 120 identification 122 refers, for example, to a cardiac phase of the patient 14.

In a detection step 124, at least a predetermined first feature 126 and a predetermined second feature 128 in each image of the first plurality 114 of first images is detected and the location of the first feature 126 is determined.

Further, as in the example with a stent, the predetermined first feature 126 comprises a marker and the predetermined second feature 128 comprises a wire, for example a guide wire for stent implanting procedures.

Further, in a tracking and registration step 127, the first and second features 126, 128 in each image of the first plurality 114 of first images are tracked. Those images are registered to one of the first images which one image 116a is determined as a reference image $116_R$. The registration is being calculated such that it corresponds to the spatial matching of the first and second features of each first image with the first and second features of the reference image. The registration is achieved with elastic restoration fields.

Further, in a decomposition step 130, the elastic restoration fields are decomposed into a combination of an affine transform and a relative elastic warping transform.

Because the detection step 124, the tracking and registration step 127 and the decomposition step 130 are directly related to each other, the steps are indicated with a common box 129 in the diagram. Further, for these steps, i.e. the detection step 124, the tracking and registration step 127 and the decomposition step 130, the received first plurality 114 of first images is provided, which is indicated with arrow 131 entering the box indicating those steps.

According to one example, the box 129 comprises the marker and wire tracking.

In a recording step 132, the relative elastic warping transform instances, or values, are recorded and tagged with a corresponding phase attribute 120, which corresponding phase attribute is derived from the phase attribute phase identifying step 122. Thus, a warping map 134 is created. The warping map provides a set of instances or values $R\phi_t$ . . . which can also be referred to as $\{R\phi_t\}$.

The entering of phase attributes is indicated by an arrow 123a entering the box indicating the recording step 132.

For the recording step 132, the results of the detection step 124, the tracking and registration step 127 and the decomposition step 130 are provided, which is indicated by an arrow 133 coming from the box 139 entering the box indicating the recording step 132.

In a generating step 136, an integrated first image 138 is generated by integrating at least two images of the first plurality 114 of first images, wherein the integration is a temporal integration. The at least two images are also elastically motion compensated. Hence, for this generating step 136, the received plurality of images 114 is provided, indicated by an arrow 137 entering the box indicating the generating step 136.

According to the exemplary embodiment shown, the method 110 relates to producing an image of the stent. The integrated first image 138, for example, is a wire based stent boost image.

In a further reception step 140, at least one secondary image 142 revealing a second criterion 119 is received, wherein a phase attribute 120 is identified and recorded for the at least one secondary image 142.

In a further detection step 146, the predetermined first feature 126 is detected in the at least one secondary image 142 and the first features 126 are tracked by determining their locations.

For the further detection step 146, the at least one secondary image 142 is provided, which is indicated by an arrow 145 entering the box indicating the further detection step 146.

Then, in a computing step 148, a first-feature-based inter-criterion transform 149 is computed for bringing the first features 126 in the reference image $116_R$ at the first features 126 in the at least one secondary image 142 into correspondence with each along time. The computing is based on the locations of the first features 126 determined in step 124 and locations of the first features 126 tracked in step 146, which is indicated by an arrow 147 entering the box indicating the computing step 148.

Further, the locations of the first features 126 in the first plurality 114 of first images are provided from detection step 124 directly or via generating step 136 to the computing step 148. This providing of the first feature locations is indicated by arrows 150a leading from the box 129 to the box indicating the generating step 136 and an arrow 150b leading from there to the box indicating the computing step 148.

In a generating step 152, a restoration transform 153 is generated by associating one of the recorded relative elastic warping transform instances or values of the warping map 134 with a phase attribute matching the phase attribute of the at least one secondary image 142 and combining the associated relative elastic warping transform with the computed first-feature-based inter-criterion transform 149.

According to an exemplary embodiment, not further shown, the restoration transform (153) is a distortion restoration transform.

According to an exemplary embodiment, not further illustrated, when building the warping map, the corresponding relative elastic transforms are averaged, for example in case several images, i.e. images corresponding to the non-consecutive frame indices $t_A$, $t_B$ etc., correspond to the same phase value $\phi$. As an advantage, only one transform for entry $\phi$ is obtained that accounts for images $t_A$, $t_B$ etc.

The relation to the phase attributes being provided by the phase attribute identifying step 122 is indicated by the arrow 123b entering the box indicating the generating step 152 from the right side. An arrow 156 entering the box indicating the generating step 152 from the left side in FIG. 2b indicates the sub-step of providing the warping map 134 with its recorded relative elastic warping transform instances or values where one of these matching with a phase attribute is chosen. The computed first-feature-based inter-criterion transform 149 is entering the generating step 152 indicated by an arrow 158 entering the box from above.

If Wt is the full elastic transform matching the wires as the second features 128 along time, and if At is the affine transform matching the markers along time, then the relative elastic warping transform is defined as $Rt=Wt*At^{-1}$. With respect to the restoration transform 153, first, based on the current cardiac phase and using the pre-contrast agent warping map 134, it is possible to retrieve the corresponding elastic transform. However, what is retrieved from the warping map 134 is the relative elastic transform $R\phi_a$. This transform is combined with the current marker matching transform At to form the restoration field: $R\phi_a*At$.

In a further generating step 160, a combined inter-criterion image 162 is generated by combining the integrated first image 138 and the at least one secondary image 142, wherein at least one of the integrated first image 138 and the at least one secondary image 142 has been transformed according to the generated restoration transform 153, which is provided as a result from the generating step 152, indicated by an arrow 159 entering the box indicating the further generating step 160. The provision of the integrated first image 138 is indicated by an arrow 161 entering the box indicating the further generating step 160.

For example, the generating step 160 comprises $R\phi_a*At$ [Image$_t$], wherein in this term, [image] can comprise the integrated first image 138 and/or the at least one secondary image 142.

For example, the result of the further generating step 160, i.e. the combined inter-criterion image 162 is then provided or output for further use, indicated by an arrow 163, for example for displaying the combined inter-criterion image 162.

One of the advantages of the above-described method is that the computing of the restoration in the generating step 152, the warping map 134 accounts for elastic transforming and the computed first-feature-based inter-criterion transform 149 accounts for affine transforming. Thus, the combined inter-criterion image 162 provides the information shown in the secondary image 142, that is for example an X-ray image, plus the information provided in the pre-boosted stent image which image has also been transformed to the actual situation in the secondary image 142. Thus, a user is provided with enhanced detailed information about the situation, for example, of a stent inserted into a vessel. The method according to the invention provides thus the advantage, that although the information about the situation of the wire, that is the second feature 128, is not visible in the secondary image 142, the so to speak missing information is nevertheless provided in the combined inter-criterion image 162, as if it was visible in the image 142.

Hence, in case the object is a patient and the region of interest relates to heart vessels, the affine transform compensates for breathing motion and translational heart motion whereas the elastic transforming compensates for bending motion due to heart motion.

From FIG. 2b, it can be seen that several steps are depending on each other, which means that some steps have to be carried out before the following steps can be performed whereas it is also visible that some steps can be carried out parallel or after others contrary to the arrangement of FIG. 2b. Because the method steps and sub-steps are indicated with boxes having round corners and indicating the data flow from one step to the other by arrows indicating the dependency of the individual steps, it becomes clear, that the generating step 136 can be carried out after the reception step 112 but before performing the generating step 160. As a further example, the generating step 136 can be carried out before or parallel to the sequence of the detection step 124, the tracking step 126, the decomposing step 130 and the recording step 132. As another example, the recording step 132 can be carried out before the generating step 152 generating the restoration transform 153. According to an exemplary embodiment, not further shown in detail, the combined inter-criterion image 162 is displayed to a user, for example displayed on the display 32 shown in FIG. 1.

According to an exemplary embodiment, the first plurality 114 of first images and the at least one secondary image 142 are acquired by X-ray images, for example by the X-ray acquisition device 16 of FIG. 1. But it is noted, that this embodiment is not further shown in FIG. 2b, but can easily be understood.

It must be noted that the further exemplary embodiments shown in FIGS. 3 to 6, the same reference numbers have been used for similar, respectively same method steps and results. Further, it is noted that only the differing or additional features of the other embodiments are described. In other words, where nothing contrary is mentioned, the embodiments have the same features and steps as described with reference to FIG. 2b.

Figure 3:
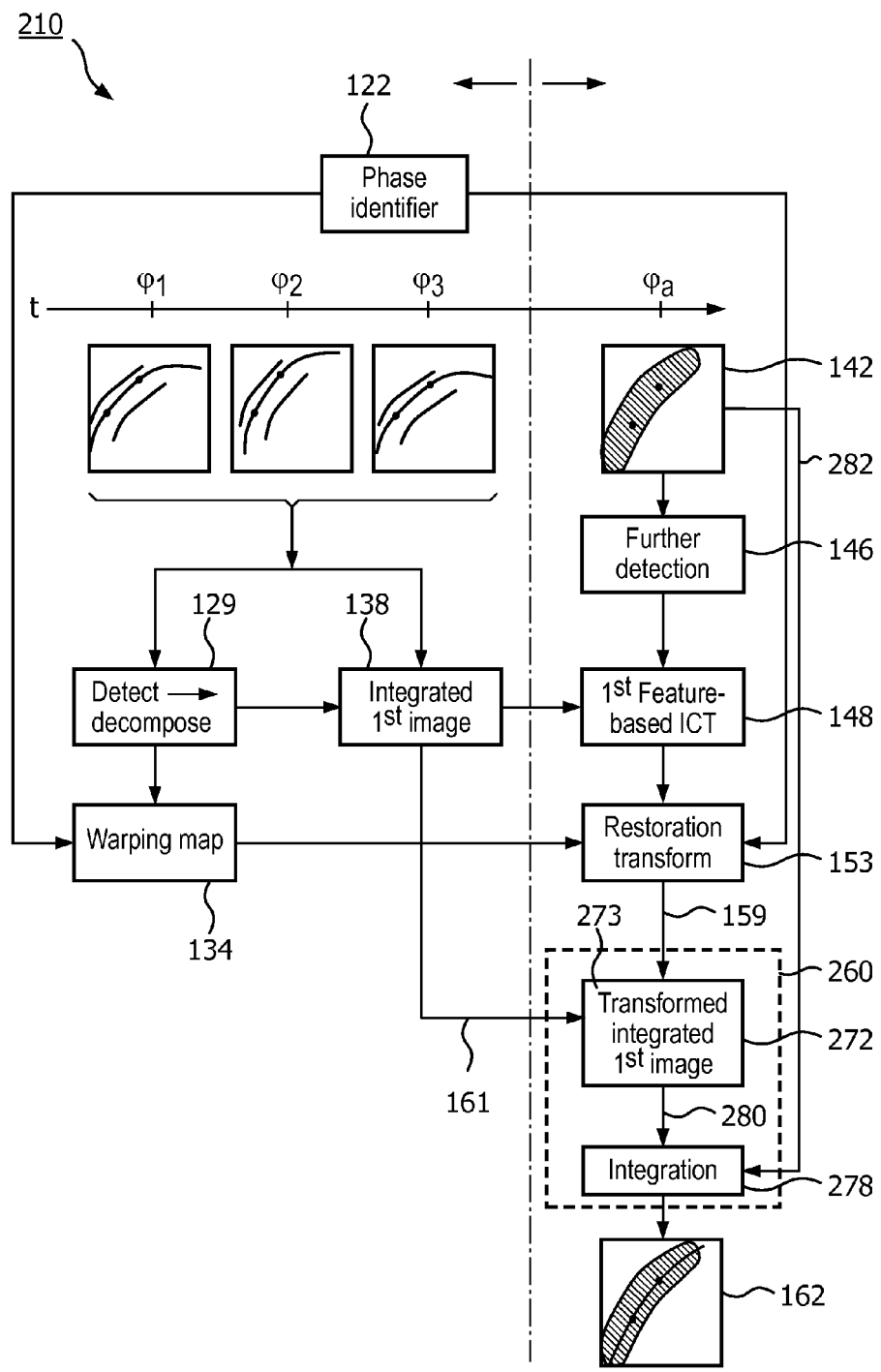
FIG. 3 schematically shows further sub-steps of a further exemplary embodiment of the method of FIG. 2b.

According to a further exemplary embodiment of a method 210, shown in FIG. 3, the generating of the combined inter-criterion image 162 is shown in detail. In a generating step 260 two sub-steps are provided: As a first sub-step, a transformation step 272 is provided in which the provided integrated first image 138 is transformed into a transformed integrated first image 273 according to the generated restoration transform 153. For the transformation step 272, the integrated first image 138 is entering the box indicating the transformation step 272 from the left-hand side via the arrow 161 and the generated restoration transform 153 is entering the box indicating the transformation step 272 from above indicated by the arrow 159.

As a second sub-step, an integration step 278 is provided in which the transformed integrated first image 273 is combined with the at least one secondary image 142. This is indicated by an arrow 280 entering the integration box 278 from above from the box indicating the transformation step 272 and an arrow 280 indicating the entering of the secondary image 142 from the right-hand side into the box indicating the integration step 278.

In other words, the generating step 260 comprises the transformation sub-step 272 and the integration sub-step 278, thus providing the combined inter-criterion image 162.

Figure 4:
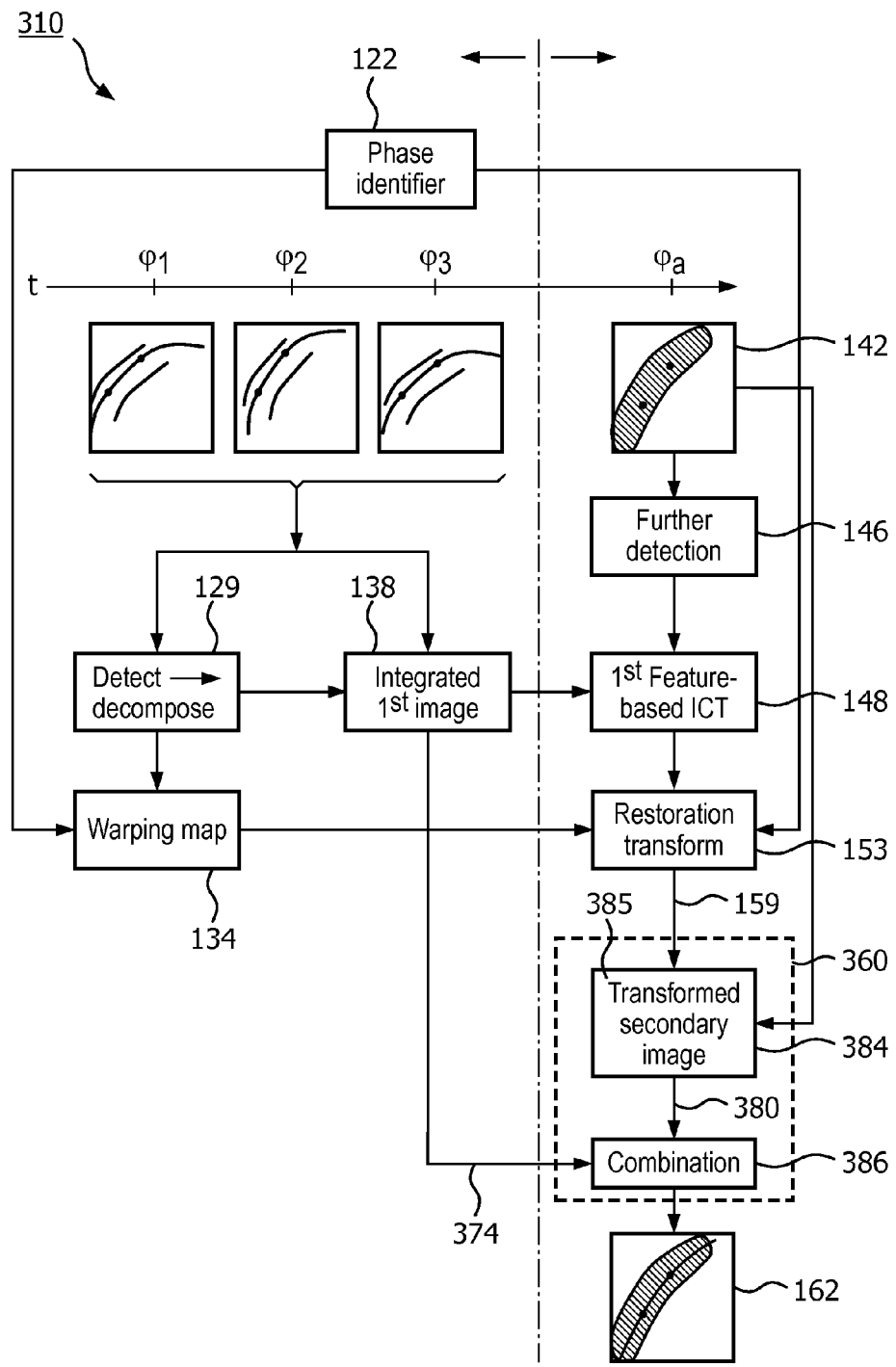
FIG. 4 schematically shows a further exemplary embodiment of the method of FIG. 2b.

According to another exemplary embodiment, a method 310 is provided which is schematically shown in FIG. 4. In this embodiment, a generating step 360 is provided comprising a first sub-step in form of a transformation step 384 in which the at least one secondary image 142 is transformed into a transformed secondary image 385 according to the generated restoration transform 153. This is indicated by the arrow 159 entering the box of the transformation step 384 from above. As a second sub-step, a combination step 386 is provided in which the transformed secondary image 385 is combined with the integrated first image 138. This is indicated by an arrow 374 entering the box indicating the combination step 386 from the left-hand side and an arrow 380 entering the box indicating the combination step 386 from above.

According to the example shown, in order to warp the vessel image, the transform must be used in the right direction. This is achieved by an "inverse" transform stored in the map. This is also achieved by directly storing the correctly directed transform.

For example, the correctly directed transform refers to transforming from the reference image to the current (or live) image or from the current image to the reference image. Of course, this can also comprise a transformation from the current image and from the reference image to a predetermined image in between.

Figure 5:
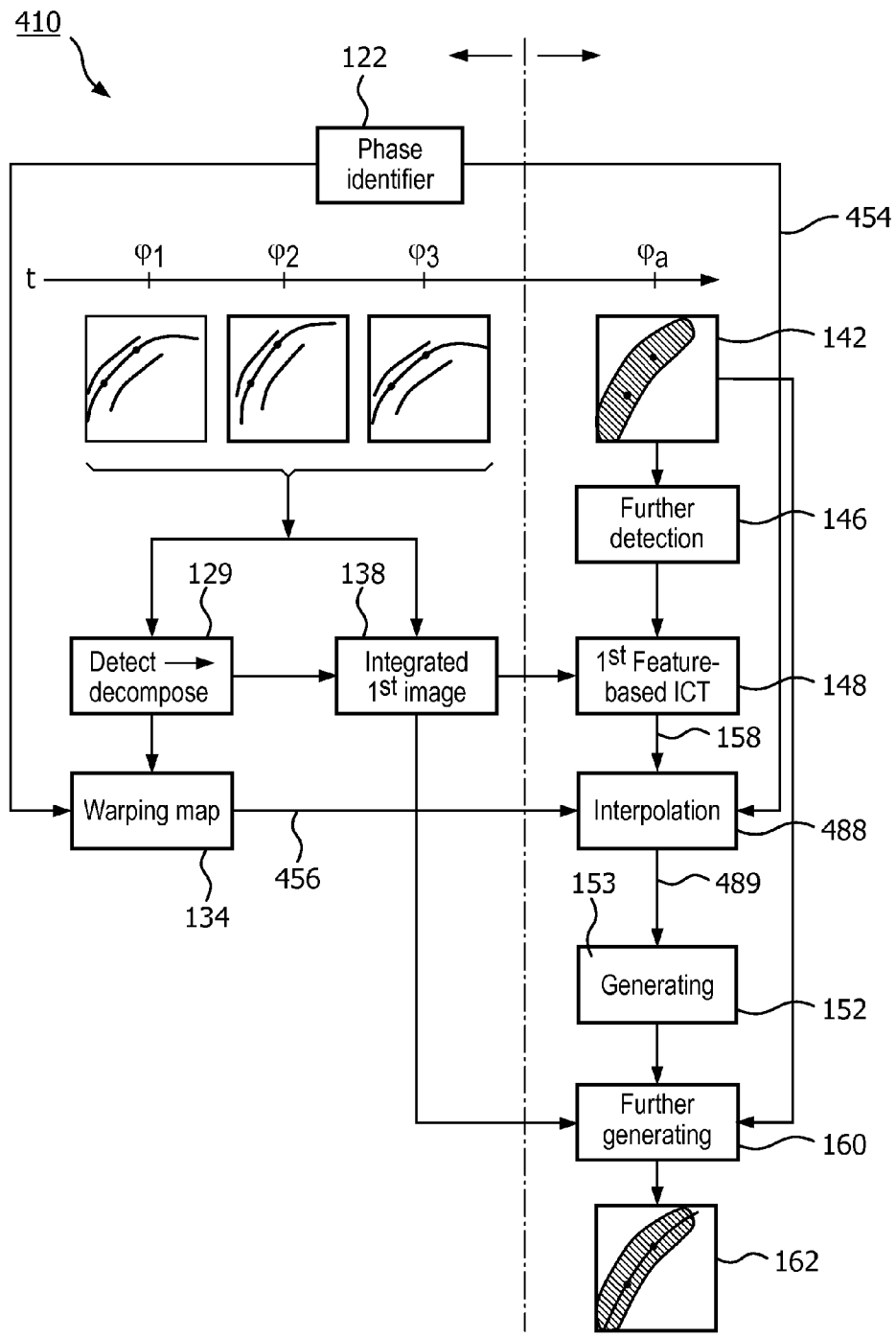
FIG. 5 schematically shows a further exemplary embodiment of the method of FIG. 2b.

According to another exemplary embodiment, the embodiments of FIGS. 3, 4, and 5 involve either some specific pre-computing in the map, or some specific computing in steps 153.

However, because inverting a transform is tedious, according to another exemplary embodiment it is provided to compute and store the needed transforms in the map.

Thus, the combined inter-criterion image 162 is generated. It must be noted that in comparison to the exemplary embodiment shown in FIG. 3, according to FIG. 4 it is the secondary image 142 that is transformed before the combination with the integrated first image 138 whereas in FIG. 3 the secondary image 142 is combined with the transformed integrated first image 138.

According to another exemplary embodiment, not further shown in detail, the at least one secondary image 142 and the integrated image 138 are both transformed according to the generated restoration transform 153. Then, the transformed images are combined with each other to generate the combined inter-criterion image 162.

According to another exemplary embodiment not further shown, the at least one secondary image 142 and the integrated image 138 are each transformed with a predetermined ratio of the generated restoration transform 153.

With reference to FIG. 5, in another exemplary embodiment a method 410 is shown, wherein for the generating step 152, at least two recorded relative elastic warping transform instances of the warping map 134 are provided to interpolation sub-step 488 according to the phase attribute 120 of the at least one secondary image 142, which phase attribute 120 is derived from the phase identifier step 122. The contribution of the phase attribute is indicated by an arrow 454 entering the box indicating the interpolation step 488 from the right side. In FIG. 5, the arrow 158 entering the box indicating the interpolation step 488 from above indicates the provision of the computed first-feature-based inter-criterion transform 149 used in the generating step 152 and not actually in the interpolation step 488. In the interpolation step 488, the at least two recorded relative elastic warping transform instances are interpolated.

The entering of the at least two recorded relative elastic warping transform values of the warping map 434 is indicated by an arrow 456. The result of the interpolation step 488 is provided to the generating step 152 which step results in the restoration transform 153. The providing of the result to the generating step 152 is indicated by an arrow 489.

The interpolation step 488 provides the possibility to get an enhanced result because even when there is no really matching value in the warping map with respect to the phase attribute of the secondary image 142, a precise value for the warping map is created by the interpolation. Thus, the restoration transform 153 generated in the generation step 152 is based on the interpolated value for the warping map 134. Thus, for generating the combined inter-criterion image 162, the warping map 134 can comprise several values without the necessity to provide a high resolution for the warping map itself.

Thus, only a reduced number of values have to be generated for the warping map, because the interpolation provides the so to speak higher resolution although the warping map has a lower resolution.

According to another exemplary embodiment of the invention, FIG. 5 describes a method 510 wherein a second plurality 543 of secondary images 542a, 542b, 542c revealing to the second criterion 119 is acquired. This second plurality 543 enters a selection step 590 where at least one image of the second plurality 543 is selected as at least one secondary image 542 used for further steps in a similar manner as described above. A phase attribute is identified and recorded for the selected at least one secondary image 542 based on the phase attribute identifying procedure 122 providing the phase attributes 120.

The selected secondary image 542 is supplied to the further steps in a similar manner as in the methods described above, in particular with reference to FIG. 2b, i.e. the secondary image 542 enters the further detection step 146 where the predetermined first features 126 are detected in the at least one secondary image 542. This is indicated by an arrow 563 entering the box indicating the detection step 146.

The secondary image 542 also enters the generating step 160 which is indicated by an arrow 561 entering the box indicating the generating step 160 from the right-hand side.

Figure 7:
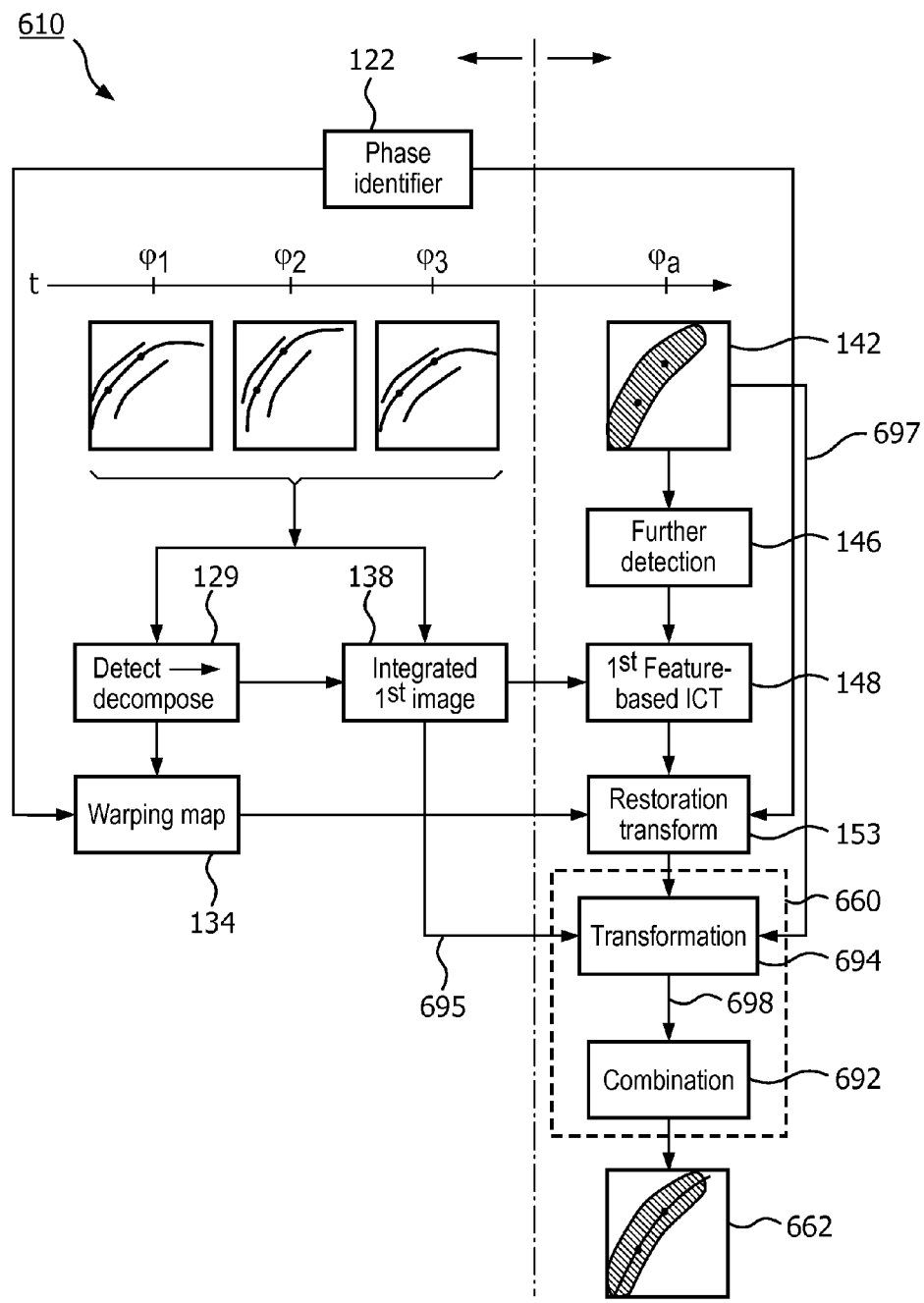
FIG. 7 schematically shows a further exemplary embodiment of the method of FIG. 2b.

FIG. 7 shows a further exemplary embodiment of a method 610, wherein a generating step 660 is provided comprising a combination 692 as a sub-step where the images are combined in a merging manner with a varying fading factor over a period of time. Prior to the combination step 692, at least one of the integrated first image 138 and the at least one secondary image 142 has been transformed in a transformation step 694 according to the generated restoration transform 153.

Thus, for the transformation step 694 the integrated first image 138 is provided, which is indicated by an arrow 695 entering the box indicating the transformation step 694 from the left side. Further, for the transformation step 694 also the secondary image 142 is provided, indicated by an arrow 697 entering the box indicating the transformation step 694 from the right side. The result of the transformation step 694 is then provided to the combination step 692 merging the images, of which at least one has been transformed, with a varying fading factor. The provision of the result is indicated by an arrow 698 entering the box indicating the combination step 692 from above. Hence, the result of the generating step 660 is a varying combined inter-criterion image 662.

According to one example, not further shown, the merging in the combination sub-step 692 comprises continuously showing one of the images while periodically fading in and out of the other one of the images.

For example, the at least one secondary image 142 is continuously shown as the transformed integrated first image is periodically fading in and out. Thus, it is ensured but no information of the secondary image 142 gets lost due to constant overlaying of the transformed integrated first image. In other words, because the secondary image 142 can be seen without any additional information periodically in between the fading in or the overlaying of the transformed integrated first image, the user gets the information that otherwise would be hidden in the combined inter-criterion image.

According to a further exemplary embodiment, not further shown, the first plurality of first images is acquired for at least one heart cycle and several different integrated first images are generated for different phases of the heart cycle. A second plurality of secondary images is acquired for at least one heart cycle and combined inter-criterion images are generated for different phases of the heart cycle. As an example, the combined inter-criterion images are displayed as a cine-loop.

An exemplary embodiment for the warping steps of a wire from one image onto another image is now described with reference to FIGS. 8 and 9.

Figure 8:
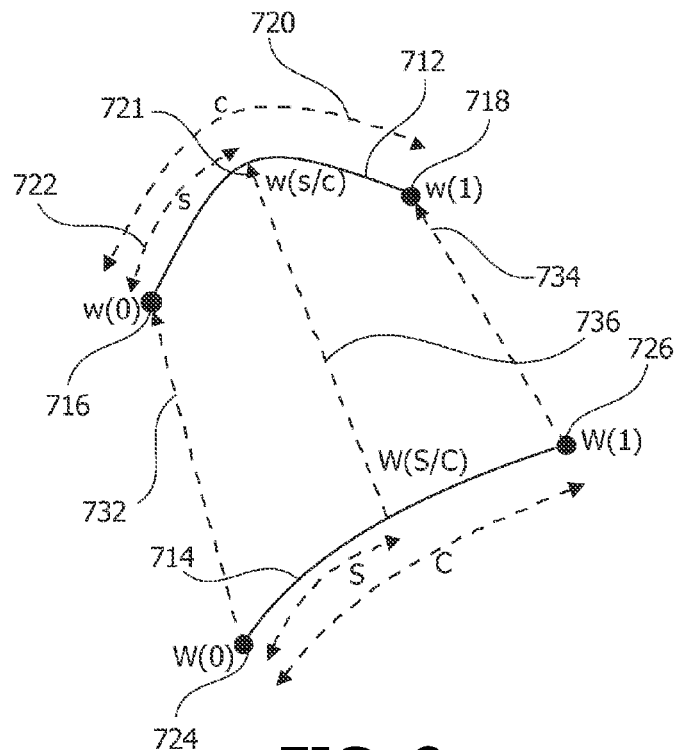
FIG. 8 schematically shows an example for matching points on a wire.

FIG. 8 schematically shows a procedure to match points on a wire, including markers. FIG. 8 shows a first wire w, indicated with reference number 712, and a second wire W, indicated with reference number 714. The first and second wires 712, 714 are two different images from the same physical wire.

The first wire 712 is defined by a first marker w(0), indicated with reference number 716, and a second marker w(1), indicated with reference number 718. A first arrow 720 indicates the distance c between the first and the second markers 716, 718 on the first wire 712. A first point 721 is indicated on the first wire 712. The distance of any point on the first wire 712 can be defined by a distance s, indicated with a second arrow 722 for the first point 721. Hence, the first point 721 on the first wire 712 is defined by w(s/c).

The second wire 714 is defined by a third marker W(0), indicated with reference number 724, and a fourth marker W(1), indicated with reference number 726. A third arrow 728 indicates the distance C between the third and the fourth markers 724, 726 on the second wire 714. A second point 729 is indicated on the second wire 714. The distance of any point on the second wire 714 can be defined by a distance S, indicated with a fourth arrow 730 for the second point 729. Hence, the second point the second wire 714 is defined by W(S/C).

The second wire 714 is warped on the first wire 712 so that:

$$s/c = S/C$$

or in another definition:

$$s = S*c/C$$

The warping is performed such that the second wire 714 (W) matches the first wire 712 (w) so that the relative distances along the wires are preserved. The warping of the second wire 714 onto the first wire 712 is indicated with three dotted arrows, one of which, indicated with 732, is leading from the third marker 724 to the first marker 716, a second, indicated with 734, is leading from the fourth marker 726 to the second marker 718 and a third, indicated with 736, is leading from the second point 729 to the first point 721.

With respect to the wire, this correctly generalizes the case of an affine transform with scaling along the inter-marker segment, i.e. the segment between the first and second markers 716, 718, respectively the third and fourth markers 724, 726.

Figure 9:
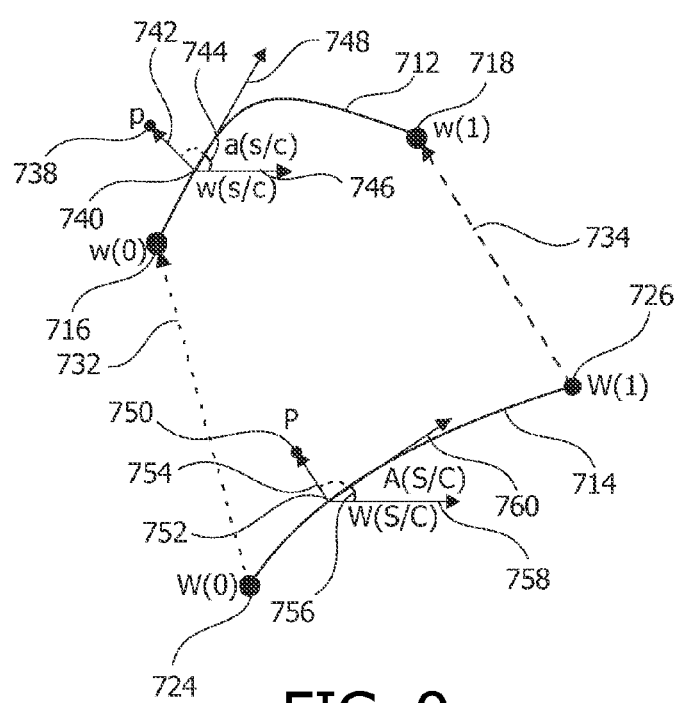
FIG. 9 shows an example for extending the wire-matching of FIG. 8 to other points in the image.

Once, the transform of the points on the wire has been computed, the warping of the so-called wire-matching is extended to other points in the image, which is described in FIG. 9.

For example, a first point p, indicated with reference number 738, is located in the surrounding of the first wire 712, but with a certain distance to the first wire 712. The first point 738 has a corresponding closest point on the first wire 712, which in the following is referred to as a second point $w_p$, indicated with reference number 740, having the closest distance to the first point 738, which distance is the orthogonal projection of the first point 738 on the first wire 712, indicated with a first distance arrow 742. A first wire angle a(s/c), referenced by 744, is defined as the angle between a horizontal line 746 and a peripheral line 748 at the second point 740, or in other words, the line perpendicular to the first distance line 742.

The peripheral line 748 can also be defined as the tangent line on the $1^{st}$ wire at point $w_p$. Further, the peripheral line 750 can also be defined as the tangent line on the $2^{nd}$ wire at point $W_p$.

With respect to the second wire 714, a third point P is indicated with reference number 750, is located in the surrounding of the second wire 714, but again with a certain distance to the second wire 714. The third point 750 has a corresponding closest point on the second wire 714, which in the following is referred to as a fourth point $W_P$, indicated with reference number 752, having the closest distance to the third point 750, which distance is the orthogonal projection of the third point 750 on the second wire 714, indicated with a second distance arrow 754. A second wire angle A(S/C), referenced by 756, is defined as the angle between a horizontal line 758 and a peripheral line 760 at the third point 752, or in other words, the line perpendicular to the first distance line 754.

For the warping, the third point 750, or point P, is mapped on point p, i.e. the first point 738, such that a point-to-wire signed distance is preserved and such that the angle with the wire is preserved. The term "signed distance" refers to taking into account the left and right sides of the wire.

This translates in:

$$p = w + R(a-A) * WP$$

where:
w is defined by s=S*c/C
WP is the vector linking W to P
R(θ) is the rotation matrix of angle θ
−w+V is the affine addition of a point and a vector According to an exemplary embodiment, correct generalization of an affine case is provided over the full image.

It is explicitly noted, that although the Figs. show different embodiments, each FIG. focusing on a specific aspect of the many aspects of the invention, the embodiments are herewith also disclosed in all possible combination.

For example, the basic method steps in FIG. 2b can be combined with the features described in relation with FIG. 3 and FIG. 4.

For example, the basic method steps in FIG. 2b, as well as the afore-mentioned combinations, can be combined with the features described in relation with FIG. 5 disclosing the interpolation.

Figure 6:
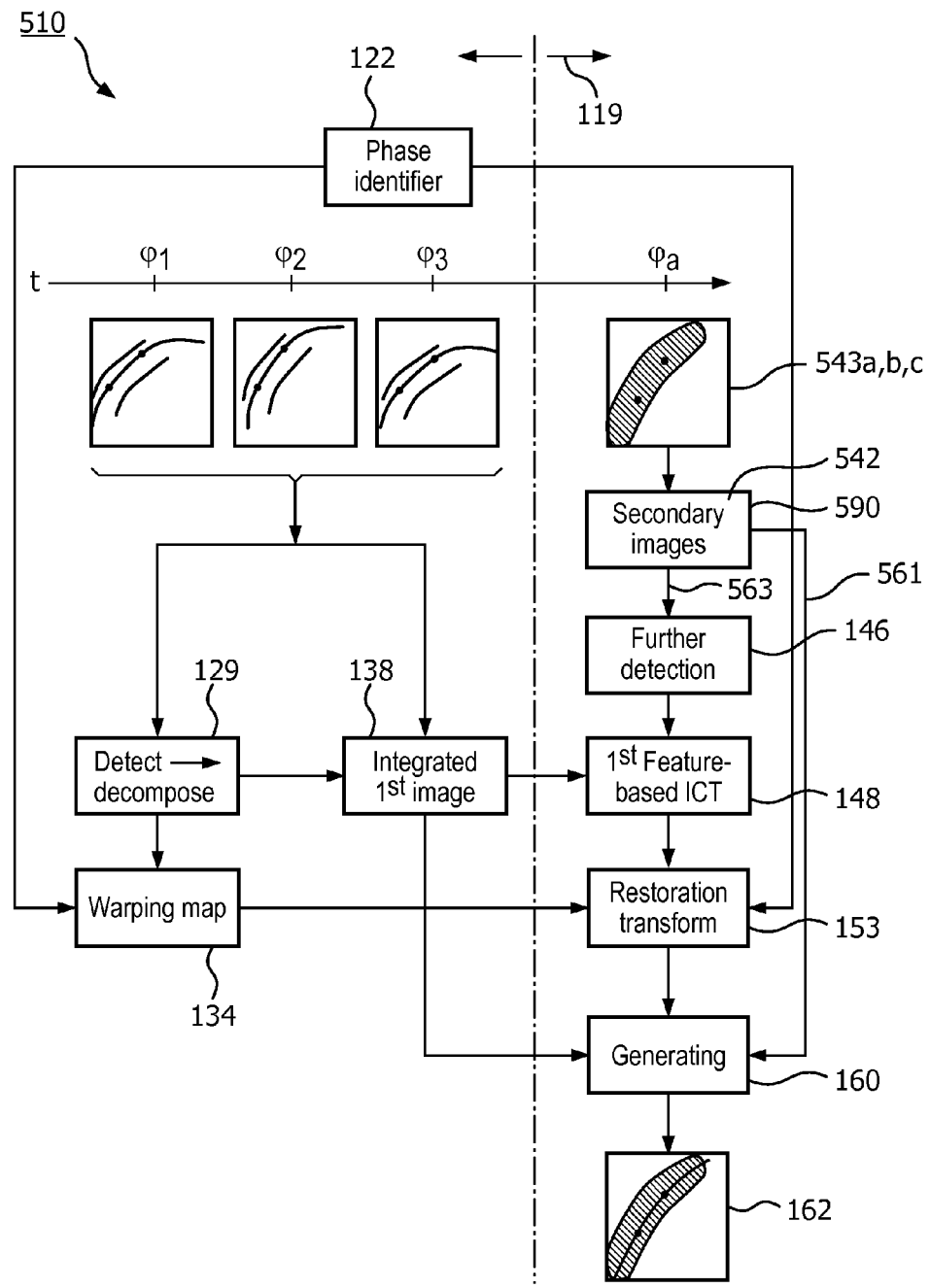
FIG. 6 schematically shows a further exemplary embodiment of the method of FIG. 2b.

For example, the basic method steps in FIG. 2b, as well as the afore-mentioned combinations, can be combined with the features of the image selection described in relation with FIG. 6.

For example, the basic method steps in FIG. 2b, as well as any of the aforementioned combinations, can be combined with the merging with a varying fading factor described in relation with FIG. 7.

As a further example, the basic method steps in FIG. 2b can be combined with the features described in FIG. 3, the features of the interpolation described in FIG. 5 and the features of the image selection described in FIG. 6.

As a still further example, the combination described before can be combined with the features of the merging with a varying fading factor described in relation with FIG. 7.

Further, it is noted that some aspects of the invention have been described with reference to the embodiments referring to method type aspects and some aspects of the invention have been described with reference to apparatus type aspects. However, a person skilled in the art will gather from the description of the embodiments that, unless other notified, in addition to any combination of features belonging to one type of subject matter also any combination between features relating to different subject matters, in particular between features of the apparatus type aspects and features of the method type aspects is herewith considered to be disclosed.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage.

A computer program may be stored and/or distributed on a suitable medium, such as an optical storage medium or a solid state medium supplied together with or as part of other hardware, but may also be distributed in other forms, such as via the internet or other wired or wireless telecommunication systems.

Any reference signs in the claims should not be construed as limiting the scope.

The invention claimed is:

1. A system for producing an image of a physical object, the system comprising:
   an image acquisition device; and
   a processing arrangement comprising a tracking unit, an association unit, a determination unit, a restoration unit and a generation unit;
   wherein the image acquisition device is configured to acquire a first plurality of first images revealing a first criterion and to acquire at least one secondary image revealing a second criterion; and
   wherein the tracking unit is configured to track a predetermined first feature and a predetermined second feature in a first plurality of first images, which images reveal a first criterion; and to track the predetermined first feature in at least one secondary image which image reveals a second criterion;
   wherein the determination unit is configured to determine a first feature transform; to determine second feature distortion vector fields relative to the first feature transform; and to determine a first-feature-based inter-criterion transform;
   wherein the association unit is configured to associate and record second feature distortion vector fields corresponding to at least two phase attributes;
   wherein the restoration unit is configured to restore current physical distortion by composing the first-feature-based inter-phase transform and the second feature distortion vector fields corresponding to a matching phase attribute; and
   wherein the generation unit is configured to generate a combined inter-criterion image based on the restored physical distortion.

2. The system according to claim 1, wherein the processing arrangement is configtired to:
   receive the acquired first plurality of first images revealing the first criterion and to identify and record a phase attribute for each image of the first plurality of images.

3. The system according to claim 2, wherein the processing arrangement is further configured to:
   detect at least the predetermined first and the predetermined second feature in each image of the first plurality of first images and to determine the location of the first feature.

4. The system according to claim 3, wherein the processing arrangement is further configured to:
   track the first and second features in each image of the first plurality of first images, and to register those images to one of the first images, which one image is determined as a reference image, said registration being calculated so that it corresponds to the spatial matching of the first and second features of each first image with the first and second features of the reference image; wherein the registration is achieved with restoration fields.

5. The system according to claim 4, wherein the processing arrangement is further configured to:
   decompose the restoration fields into a combination of an affine transform and a relative warping transform.

6. The system of claim 5, wherein the processing arrangement is further configured to:
   record the relative warping transform instances and to tag them with a corresponding phase attribute, wherein a warping map is created.

7. The system of claim 6, wherein the processing arrangement is further configured to:
   generate an integrated first image by integrating at least two images of the first plurality of first images, wherein the integration is a temporal integration; and wherein the at least two images are motion-compensated.

8. The system of claim 7, wherein the processing arrangement is further configured to:
   receive the at least one secondary image revealing the second criterion and to identify and record a phase attribute for the at least one secondary image.

9. The system according to claim 8, wherein the processing arrangement is configured to interpolate at least two recorded relative warping transform instances of the warping map according to the phase attribute of the at least one secondary image.

10. The system of claim 8, wherein the processing arrangement is further configured to:
    detect the first feature in the at least one secondary image and to track the first features by determining their locations.

11. The system of claim 10, wherein the processing arrangement is further configured to:
    compute the first-feature-based inter-criterion transform for bringing the first features in the integrated image and the first features in the at least one secondary image into correspondence with each other along time, wherein the computing is based on the locations of the first features determined before and the locations of the first features tracked before.

12. The system of claim 11, wherein the processing arrangement is further configured to:
    generate a restoration transform, for restoring the current physical distortion, by associating one of the recorded relative elastic warping transform instances of the warping map with a phase attribute matching the phase attribute of the at least one secondary image and composing the associated relative warping transform with the computed first-feature-based inter-criterion transform.

13. The system of claim 12, wherein the processing arrangement is further configured to:
    generate the combined inter-criterion image by combining the integrated first image and the at least one secondary image, wherein at least one of the integrated first image and the at least one secondary image has been transformed according to the generated restoration transform.

14. The system of claim 1, the determining of said first feature transform being based on said predetermined second feature.

15. The system of claim 14, the determining of a field from among said second feature distortion vector fields being based upon the determined first feature transform.

16. The system according to claim 1, comprising a display configured to display the combined inter-criterion image.

17. The system according to claim 1, wherein the image acquisition device is an X-ray image acquisition device; and wherein the first plurality of first images and the at least one secondary image are X-ray images.

18. A method for producing an image of a physical object, the method comprising the following steps:
   a) tracking a predetermined first feature and a predetermined second feature in a first plurality of first images, which images reveal a first criterion;
   determining a first feature transform; and determining second feature distortion vector fields relative to the first feature transform;
   b) associating and recording second feature distortion vector fields corresponding to at least two phase attributes;
   c) tracking the predetermined first feature in at least one secondary image which image reveals a second criterion;
   d) determining a first-feature-based inter-criterion transform;
   e) restoring current physical distortion by composing the first-feature-based inter-phase transform and the second feature distortion vector fields corresponding to a matching phase attribute; and
   f) generating a combined inter-criterion image based on the restored physical distortion.

19. The method according to claim 18,
   wherein step a) comprises the following sub-steps:
      a1) receiving the first plurality of first images revealing the first criterion; identifying and recording the phase attribute for each image of the first plurality of first images;
      a2) detecting at least the predetermined first feature and the predetermined second feature in each image of the first plurality of first images and determining the location of the first feature; a3) tracking the first and second features in each image of the first plurality of first images, and registering those images to one of the first images, which one image is determined as a reference image, said registration being calculated so that it corresponds to the spatial matching of the first and second features of each first image with the first and second features of the reference image;
   wherein the registration is achieved with restoration fields;
      a4) decomposing the restoration fields into a combination of an affine transform and a relative warping transform; and
      a5) generating an integrated first image by integrating at least two images of the first plurality of first images; wherein the integration is a temporal integration; and wherein the at least two images are motion-compensated;
   wherein step b) comprises:
      recording the relative warping transform instances as the second feature distortion vector fields and tagging them with a corresponding phase attribute; and wherein a warping map is created;
   wherein step c) comprises the following sub-steps:
      c1) receiving the at least one secondary image revealing the second criterion; wherein a phase attribute is identified and recorded for the at least one secondary image; and
      c2) detecting the first feature in the at least one secondary image and tracking the first features by determining their locations;
   wherein step d) comprises computing the first-feature-based inter-criterion transform for bringing the first features in the integrated image and the first features in the at least one secondary image into correspondence with each other along time; wherein the computing is based on the locations of the first features determined in step a2) and the locations of the first features tracked in step c2);
   wherein, for restoring the current physical distortion, step e) comprises generating a restoration transform by associating one of the recorded relative warping transform instances of the warping map with a phase attribute matching the phase attribute of the at least one secondary image and composing the associated relative warping transform with the computed first-feature-based inter-criterion transform; and
   wherein step f) comprises generating the combined inter-criterion image by combining the integrated first image and the at least one secondary image, wherein at least one of the integrated first image and the at least one secondary image has been transformed according to the generated restoration transform.

20. The method according to claim 19, wherein in step f) the integrated first image is transformed according to the generated restoration transform; and wherein the transformed integrated first image is combined with the at least one secondary image.

21. The method according to claim 19, wherein before step e) at least two recorded relative warping transform instances of the warping map are interpolated according to the phase attribute of the at least one secondary image.

22. The method according to claim 18, wherein before step c1) a second plurality of secondary images revealing the second criterion is acquired; and wherein at least one image of the second plurality is selected as the at least one secondary image.

23. The method according to claim 18, wherein step f) comprises combining the images in a merging manner with a varying fading factor over a period of time.

24. The method according to claim 18, wherein the first plurality of first images and the at least one secondary image are X-ray images.
   generate an integrated first image by integrating at least two images of the first plurality of first images, wherein the integration is a temporal integration; and wherein the at least two images are motion-compensated.

25. A non-transitory computer readable medium embodying a program for producing an image of a physical object, said program having instructions executable by a processor for performing a plurality of acts. among said acts there being the acts of:
   a tracking a predetermined first feature and a predetermined second feature in a first plurality of first images, which images reveal a first criterion; determining a first feature transform: and determining second feature distortion vector fields relative to the first feature transform;
   b) associating and recording second feature distortion vector fields corresponding to at least two phase attributes;
   c) tracking the predetermined first feature in at least one secondary image which image reveals a second criterion;
   d) determining a first-feature-based inter-criterion transform;
   e) restoring current physical distortion by composing the first-feature-based inter-phase transform and the second feature distortion vector fields corresponding to a matching phase attribute; and f) generating a combined inter-criterion image based on the restored physical distortion.

* * * * *